United States Patent [19]

Kobayashi et al.

[11] Patent Number: 4,732,736

[45] Date of Patent: Mar. 22, 1988

[54] ANALYTICAL ELEMENT FOR THE DETECTION HYDROGEN PEROXIDE

[75] Inventors: Morio Kobayashi, Sagamihara; Kenichiro Okaniwa, Shiroyama; Mikio Koyama, Tokorosawa; Kunihiro Furukawa, Urawa; Soichi Zanma, Kawaguchi, all of Japan

[73] Assignees: Konishiroku Photo Industry Co., Ltd.; Chugai Seiyaku Kabushiki Kaisha, both of Tokyo, Japan

[21] Appl. No.: 798,562

[22] Filed: Nov. 15, 1985

[30] Foreign Application Priority Data

Nov. 20, 1984 [JP] Japan .................. 59-243277

[51] Int. Cl.$^4$ .................. C12Q 1/28; G01N 21/77; G01N 31/22
[52] U.S. Cl. .................. 422/56; 422/57; 422/58; 436/135; 436/170; 436/904; 435/28; 435/805
[58] Field of Search .................. 436/135, 170, 904; 422/56, 57, 58; 435/28, 805

[56] References Cited

U.S. PATENT DOCUMENTS

| Re. 30,267 | 5/1980 | Bruschi | 422/58 X |
| 4,418,037 | 11/1983 | Katsuyama et al. | 436/135 X |
| 4,439,527 | 3/1984 | Pakebusch et al. | 436/135 |
| 4,478,942 | 10/1984 | Katsuyama et al. | 436/170 X |
| 4,492,754 | 1/1985 | Träger et al. | 422/56 X |
| 4,567,136 | 1/1986 | Okaniwa et al. | 422/57 X |
| 4,567,139 | 1/1986 | Batz | 436/135 X |
| 4,587,100 | 5/1986 | Amano et al. | 422/56 |

FOREIGN PATENT DOCUMENTS

| 57-94653 | 6/1982 | Japan . |
| 57-94655 | 6/1982 | Japan . |
| 2095401 | 9/1985 | United Kingdom | 436/135 |

Primary Examiner—Barry S. Richman
Assistant Examiner—J. Johnston
Attorney, Agent, or Firm—Frishauf, Holtz, Goodman & Woodward

[57] ABSTRACT

An analytical element for the detection of hydrogen peroxide comprising a peroxidase-functional material, a hydrogen donor and a coupler, wherein the peroxidase-functional material and hydrogen donor are arranged so as to be separate from each other, for example in separate layers, but are made interactive by the application of a fluid sample.

11 Claims, 1 Drawing Figure

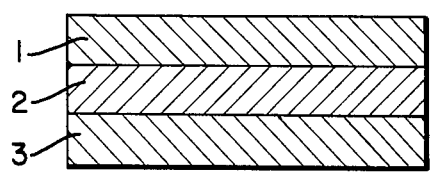

ANALYTICAL ELEMENT FOR THE DETECTION HYDROGEN PEROXIDE

BACKGROUND OF THE INVENTION

The present invention relates to an analytical element for the detection of hydrogen peroxide, and more particularly to an analytical element improved in shelf life, i.e., stability during storage, for use in quantitative analysis for of hydrogen peroxide, which analysis is carried out by measuring the dye produced during the oxidation-condensation reaction of a hydrogen donor with a coupler for preparing dyes in the presence of a peroxidase-functional material.

Various attempts have hitherto been made to improve the stability of those reagents used for such analytical elements in the dry process. Particularly, in multilayer analytical elements for analyzing for hydrogen peroxide, attempts for improving the stability of peroxidase have been proposed. For example, for the purpose of improving the stability of peroxidase, Japanese Patent Publication Open to Public Inspection (hereinafter referred to as Japanese Patent O.P.I. Publication) Nos. 50393/1979 and 116258/1982 propose the addition of certain copolymers to reagent layers, and Japanese Patent O.P.I. Publication No. 174099/1982 proposes the addition of pyrogallol derivatives to reagent layers.

These proposals, although useful as means for restraining the deterioration of peroxidase during its storage, are hardly considered satisfactory enough for preserving the ability of the element to analyze, and thus are desired to be further improved.

SUMMARY OF THE INVENTION

It is therefore an object of the present invention to provide an analytical element which is improved in stability and which is for use in the detection of hydrogen peroxide using a peroxidase-functional material, a hydrogen donor and a coupler.

To summarize, this invention is an analytical element for the detection of hydrogen peroxide; comprising a peroxidase-functional material, a hydrogen donor and a coupler, wherein the peroxidase-functional material and the hydrogen donor are arranged so as to be separate from each other but are made interactive by the application of a fluid sample.

In other words, according to the present invention, a peroxidase-functional material and a hydrogen donor are arranged to be substantially separate from each other until the time of applying a fluid sample thereto, whereby the analytical element is improved conspicuously in storage stability as compared to one containing both materials present together.

BRIEF DESCRIPTION OF THE DRAWING

The single drawing shows a multi-layer analytical element according to the invention having a first reagent layer 1, a second reagent layer 2 and a support layer 3.

The invention requires that the peroxidase-functional material reagents and the hydrogen donor reagents, required for the detection of hydrogen peroxide, be kept separate until the application of an aqueous fluid sample. In the device shown in the single FIGURE, one of these reagents is contained in reagent layer 1 and the other is contained in reagent layer 2. When the sample to be tested is applied to the test device the aqueous solvent for the test sample causes mixing of the reagents.

DETAILED DESCRIPTION OF THE INVENTION

Those peroxidase-functional materials include the conventionally known peroxidase extracted from various living things, synthetic peroxidase, other chemical substances having peroxidase-like function and extracted from living things, and the like. Of these, peroxidase is preferred. The peroxidase-functional material may be used in quantities as from 100 to 1,000,000 $U/m^2$, and preferably in the range of from 1,000 to 100,000 $U/m^2$, U being the international unit which is the amount for decomposing one mole of substrate per minute.

Examples of the hydrogen donor include 4-substituted antipyrins as disclosed in Japanese Patent O.P.I. Publication No. 52158/1973, 2-hydrazonobenzothiazolines as disclosed in Japanese Patent O.P.I. Publication No. 20471/1980, p-halogenophenols as described in Japanese Patent O.P.I. Publication No. 148100/1980 (also see Japanese Patent O.P.I. Publication No. 174099/1982 for the above), and o- or p-phenylenediamine-type compounds including those described in, i.e., Japanese Patent O.P.I. Publication Nos. 137192/1975, 94653/1982 and its corresponding U.S. Pat. No. 4,567,136 and 174099/1982.

Of these the preferred material are the 4-substituted antipyrins and p-phenylenediamine-type compounds, and particularly 4-aminoantipyrin and the p-phenylenediamine-type compounds exemplified in Japanese Patent O.P.I. Publication No. 94653/1982 and its corresponding U.S. Pat. No. 4,567,136 are preferred. These latter are represented by the formula:

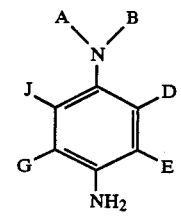

wherein A and B represent hydrogen atoms or alkyl groups, and may form a heterocyclic ring together with a nitrogen atom; D, E, G and J represent hydrogen atoms, halogen atoms, hydroxy groups, amino groups, alkoxy groups, acylamide groups, arylsulfonamide groups, alkylsulfonamide groups or alkyl groups.

Any of these hydrogen donors may be used in quantities from 0.01 to 100 millimoles/$m^2$, and preferably in the range of from 0.05 to 50 millimoles/$m^2$.

Examples of the foregoing coupler include acylacetamide compounds as disclosed in Japanese Patent O.P.I. Publication No. 94654/1982, pyrazolone-type compounds as disclosed in Japanese Patent O.P.I. Publication Nos. 94656/1982 and 174099/1982, phenol-type compounds including those disclosed in, e.g., U.S. Pat. No. 4,567,136 and Japanese Patent O.P.I. Publication Nos. 94653/1982 and 174099/1982, naphthol-type compounds as disclosed in Japanese Patent O.P.I. Publication Nos. 94655/1982 and 174099/1982, and N,N-disubstituted aniline compounds as disclosed in Japanese Patent O.P.I. Publication No. 174099/1982. The preferred among these compounds are the pyrazolone-type, phenol-type and naphthol-type compounds, of which, particularly, the compounds including those exemplified in, e.g., Japanese Patent O.P.I. Publication Nos. 94656/1982, 94653/1982, (corresponding to U.S. Pat. No. 4,567,136) and 94655/1982 and 174099/1982, and 2-tetrafluoroethylcarbonylamino-5-[α-(2,4-di-t-amylphenoxy)-pentylcarbonylamino]phenol are preferred.

Compounds disclosed in Japanese Patent O.P.I. Publication No. 94653/1982 and its corresponding U.S. Pat. No. 4,567,136 which are suitable couplers for use in the present invention, include:

(1-1) 2,4-dichloro-3-methyl-6-[α-(2,4-di-t-amylphenoxy)butylamido]phenol;
(1-2) 2-(α,α,β,β-tetrafluoropropionamido)-4-β-chloroethoxy-5-[α-(2,4-di-t-amylphenoxy)-butylamido]phenol;
(1-3) 2-chloro-3-methyl-4-ethylcarbamoylmethoxy-6-[α-(2,4-di-t-amylphenoxy)butylamido]phenol;
(1-4) 2-chloro-3-methyl-4-methoxycarbonylmethoxy-6-[α-(2,4-di-t-amylphenoxy)butylamido]phenol;
(1-5) 2-chloro-3-methyl-4-carboxymethoxy-6-[α-(2,4-di-t-amylphenoxy)butylamido]phenol;
(1-6) 2-chloro-3-methyl-4-(p-carbomethoxyphenylcarbamoylmethoxy)-6-[α-(2,4-di-t-amylphenoxy)-butylamido]phenol;
(1-7) 2-chloro-3-methyl-4-tri-ethoxycarbonylmethoxy-6-[α-(2,4-di-t-amylphenoxy)ethylamido]phenol;
(1-8) 2-chloro-3-methyl-4-methoxyethylaminocarbonylmethoxycarbonylmethoxy-6-[α-(2,4-di-t-amylphenoxy)butylamido]phenol;
(1-9) 2,4-dichloro-3-methyl-6-[3-(4-dodecylbenzenesulfonamido)benzamido]phenol;
(1-10) 2,4-dichloro-3-methyl-6-(ω-monohydrooctafluoropentanoylamino)phenol;
(1-11) 2,4-dibromo-3-methyl-6-(n-octadecanoylamino)-phenol;
(1-12) 2-(n-octylcarbonylamino)-4-chloro-5-[α-(2,4-di-t-amylphenoxy)ethylamido]phenol;
(1-13) 2-(ω-monohydro-octafluoropentanoylamino)-4-chloro-5-[α-(2,4-di-t-amylphenoxy)butylamido]phenol;
(1-14) 2-(107 -monohydro-octafluoropentanoylamino)-4-chloro-5-[α-(2,4-di-t-amylphenoxy)-acetoamino]phenol;
(1-15) 2-n-octafluorobutylcarbonylamino-5-[3-(3-pentadecanylphenoxy)propylcarbonylamino]-phenol;
(1-16) 2-n-octafluorobutylcarbonylamino-5-(2-n-lauryl-2-hydroxycarbonylethylcarbonylamino)-phenol;
(1-17) 2-(n-heptanylcarbonylamino(-5-[α-(2,4-di-t-amylphenoxy)butylamido]phenol;
(1-18) 2-(n-octafluorobutylcarbonylamino)-5-[α-(2,4-di-t-amylphenoxy)hexanoylamino]phenol;
(1-19) 2-(n-hexafluoropropylcarbonylamino)-5-[α-(2,4-di-t-amylphenoxy)pentylcarbonylamino]-phenol;
(1-20) 2-tetrafluoroethylcarbonylamino-5-[α-(2,4-di-t-amylphenoxy)propylcarbonylamino]phenol;
(1-21) 2-[α-(2,4-di-t-amylphenoxy)propylcarbonylamino-5-methyl]phenol;
(1-22) 2-[α-(2,4-di-t-amylphenoxy)propylcarbonylamino]phenol;
(1-23) 2-tetrafluoroethylcarbonylamino-5-methylphenol;
(1-24) 2-tetrafluoroethylcarbonylamino-5-n-pentadecanylphenol;
(1-25) 2-n-octafluorobutylcarbonylamino-5-[α-(2,4-di-t-amylphenoxy)methylcarbonylamino]phenol;
(1-26) 2-trifluoromethyl-6-n-undecanylcarbonylaminophenol;
(1-27) 2-phenyl-di-fluoromethyl-4-chloro-6-n-undecanylcarbonylaminophenol;
(1-28) 2-chloro-3-methyl-4-methanesulfonyloxy-6-(m-n-dodecanyloxyphenylcarbonylamino)phenol;
(1-29) 2-trifluoromethyl-4-methanesulfonylamido-6-(n-undecanylcarbonyl-N-methyl-amino)phenol;
(1-30) 2-chloro-3-methyl-4-(α-phenyl-α-carboxymethoxy)-6-[α-(2,4-di-t-butylphenoxy)butylamido]phenol;
(1-31) 2-chloro-3-methyl-4-n-octadecanyloxycarbonylmethoxy-6-phenylcarbonylaminophenol.

Compounds disclosed in Japanese Patent O.P.I. Publication No. 94655/1982 which are suitable couplers for use in the present invention include:

(1-1) 1-hydroxy-4-(3-nitrophenylsulfonamide)-N-(δ-(2,4-di-amylphenoxy)butyl)-2-naphthoamide;
(1-2) 1-hydroxy-4-((β-methoxyethyl)carbamoyl)methoxy-N-(δ-(2,4-di-amylphenoxy)butyl)-2-naphthoamide;
(1-3) 1-hydroxy-4-(isopropylcarbamoyl)-methoxy-N-dodecyl-2-naphthoamide;
(1-4) 1-hydroxy-4-(4-nitrophenylcarbamoyl)oxy-N-(δ-(2,4-di-amylphenoxy)butyl)-2-naphthoamide;
(1-5) 1-hydroxy-N-dodecyl-2-naphthoamide;
(1-6) 1-hydroxy-(4-nitro)phenoxy-N-(δ-(2,4-di-amylphenoxy)butyl]-2-naphthoamide;
(1-7) 1-hydroxy-4-(1-phenyl-5-tetrazolyloxy)-N-(δ-(2,4-di-amylphenoxy)butyl)-2-naphthoamide;
(1-8) 1-hydroxy-N-(δ-(2,4-di-amylphenoxy)butyl)-2-naphthoamide;
(1-9) 1-hydroxy-4-benzoylmethoxy-N-(δ-(2,4-di-amylphenoxy)butyl)-2-naphthoamide;
(1-10) 1-hydroxy-4-anilinocarbonylmethoxy-N-(δ-(2,4-di-amylphenoxy)butyl)-2-naphthoamide;
(1-11) 1-hydroxy-4-phenoxycarbonylmethoxy-N-(δ-(2,4-di-amylphenoxy)butyl)-2-naphthoamide;
(1-12) 1-hydroxy-4-(4-nitrophenoxycarbonylmethoxy-N-(δ-(2,4-di-amylphenoxy)butyl)-2-naphthoamide;
(1-13) 1.3-bis-(4-hydroxy-3-n-dodecylcarbamoyl-1-naphthyloxyacetoamide)benzene;
(1-14) 1.3-bis-(4-hydroxy-3-(N-(δ-(2,4-di-amylphenoxy)butyl)carbamoyl)-1-naphthylacetoamide)ethane;
(1-15) 1-hydroxy-4-chlorobenzoylmethoxy)-n-dodecyl-2-naphthoamide;
(1-16) 1-hydroxy-4-benzylaminocarbonylmethoxy-N-(δ-(3-n-dodecyloxyphenoxy)butyl)-2-naphthoamide;
(1-17) 1-hydroxy-4-(ethoxycarbonylmethoxy-N-(δ-(2,4-di-amylphenoxy)butyl)-2-naphthoamide;
(1-18) 1-hydroxy-4-ethylaminocarbonylmethoxy-N-(β(4-n-lauroylamidephenyl)ethyl-2-naphthoamide;
(1-19) bis-(4(4-hydroxy-3-(N-(β-(4-n-lauroylamidephenyl)ethyl)carbamoyl-1-naphthyloxyacetyloxy)-phenyl)methane
(1-20) 1-hydroxy-N,N-dioctadecyl-2-naphthoamide;
(1-21) 1,4-phenylenebis-(1-hydroxy-4-anilinocarbonylmethoxy-2-naphthoamide;
(1-22) 1-hydroxy-4-phenylthiocarbonylmethoxy-N-(δ-(2,4-di-amylphenoxy)butyl)-2-naphthoamide;
(1-23) 1-hydroxy-4-(4-aminoanilinocarbonylmethoxy-N-(2-n-tetradecyloxyphenyl)-2-naphthoamide;
(1-24) 1-hydroxy-N-(δ-(3-n-dodecyloxyphenoxy)butyl)-2-naphthoamide;
(1-25) 1-hydroxy-N-(β-(4-lauroylamidephenyl)ethyl)-2-naphthoamide;
(1-26) 1-hydroxy-N-(2-n-tetradecyloxyphenyl)-2-naphthoamide.

Any of these couplers may be used in quantities from 0.1 to 100 millimoles/m$^2$, and preferably in the range of from 0.5 to 50 millimoles/m$^2$.

The analytical element of this invention is prepared by coating on a support, in order from the support side, at least one reagent layer comprising at least one reagent which reacts with the component of a fluid sample and a hydrophilic colloid, and then a spreading layer which serves for permeating the component of the above fluid sample into the reagent layer.

The support to be used in this invention may be any of those conventionally used. Those suitably usable are to be liquid-impervious but light-pervious materials including various polymer materials such as polyethylene terephthalate, polycarbonate, polystyrene, and the like. Further, in addition to these materials, an inorganic material such as glass may also be used. The thickness of the support used in this invention may be discretional, and preferably from about 50 $\mu$m to about 250 $\mu$m. One side as the observation side of the support of this invention is allowed to be subjected to an arbitrary treatment according to the purposes for which it is used. Further, on the reagent-layer-to-be-provided side of the support may, if necessary, be coated a light-pervious subbing layer to improve the adhesiveness of the reagent layer to the support.

The spreading layer of the present invention is desirable to be one having (1) a function of distributing uniformly a fixed amount of a fluid sample in a fixed quantity per unit area into the reagent layer, (2) a function of removing an analytical reaction-impairing substance or factor of a fluid sample, i.e., the characteristic as described in Japanese Patent Examined Publication No. 21677/1978, and/or (3) a background function to reflect the measuring transmitted through the support when performing a spectrophotometric analysis. Accordingly, the spreading layer of this invention is allowed to be either one layer having the above function (1) alone or layers having the combined functions (1) and (2) and/or (3). Alternatively, the plurality of functions including (1) may be arbitrarily separated, and the respective functions having independent layers must be used. Further, of the functions (1), (2) and (3) any two functions may be provided to one layer and the remaining one to another layer, and the layers may be used in combination. These spreading layers include, for example, spreading layers of nonfiber porous medium called "blush polymer" composed of titanium dioxide and cellulose diacetate as described in the foregoing Japanese Patent Examined Publication No. 21677/1978; fabric spreading layers treated to be hydrophilic as described in Japanese Patent O.P.I. Publication No. 164356/1980; fiber-structure spreading layers as described in Japanese Patent O.P.I. Publication Nos. 94658/1982, 125847/1982, 197466/1982 and 70161/1983; and particles-combined-structure spreading layers as described in Japanese Patent O.P.I. Publications No. 90167/1983. Particularly the above-mentioned fiber-structure and particles-combined-structure spreading layers are very useful as materials capable of rapidly transferring blood-cell part also. The thickness of the spreading layer of the analytical element of this invention is to be determined according to the degree of the gap inside the structure, but preferably from about 100 $\mu$m to about 500 $\mu$m, and more preferably from about 150 $\mu$m to 350 $\mu$m. And the degree of the gap is preferably from about 20% to about 85%.

The reagent layer of this invention is one composed of a hydrophilic binder, which may contain the reagents of this invention, i.e., a peroxidase-functional material, a hydrogen donor and a coupler.

According to the object of this invention, it is necessary to take an embodiment wherein the peroxidase-functional material and the hydrogen donor are substantially separate from each other prior to the application of an aqueous fluid sample.

The incorporation of the above two different reagents into the reagent layer, in order to avoid undesirable mixing of the reagents before the application of the aqueous fluid sample, may be carried out by separating the layer into two adjacent layers for the respective reagent or more layers including another layer put in therebetween.

An important point in this instance is the characteristic of the binder constituting the above reagent layers. The binder used in the support layer of the above-mentioned reagent layers is desirable to be coated by use of a solvent in which the binder for the lower layer is insoluble. Namely, it is desirable to use a combination of different binders, a solvent for the upper layer's one of which binders does not dissolve the other of the lower layer. For example, a combination of a water-soluble polymer binder for the lower layer with a hydrophilic and organic solvent-soluble polymer binder for the upper layer is desirable.

More particularly, those suitable binders for the lower layer include gelatin; gelatin derivatives such as phthalated gelatin; water-soluble cellulose derivatives such as hydroxyethyl cellulose, sodium carboxymethyl cellulose, etc.; polyvinyl alcohols, polyacrylamides, polymethacrylamides, poly(mono- or dialkyl-substituted)acrylamides, poly(mono- or dialkyl-substituted)methacrylamides and water-soluble copolymers of these compounds; and the like. Those binders useful for the upper layer include poly(N-vinyl-pyrrolidone), poly(N-vinylimidazole), poly(N-vinyl-triazole), and derivatives or copolymers of these compounds; ethyl cellulose, methyl cellulose, etc.; and the like. These polymers are hydrophilic high-molecular materials soluble principally in alcohols such as ethanol, propanol, butanol, etc.

The peroxidase-functional material and the hydrogen donor are separated from each other, either one of which is incorporated into any one of the layers in a manner of dissolution or dispersion and the other is incorporated into another layer. In this instance, the coupler of this invention may be contained in either one of the layers or in both layers, or further in another layer, and therefore the position of the coupler is not restricted.

As another embodiment, either one of the peroxidase-functional material and hydrogen donor may be incorporated into the spreading layer, and the other into the reagent layer. In this case, the incorporation into the spreading layer may be carried out by various methods including dissolution, dispersion, impregnation, and the like. Particularly, in the case of the fiber-structure spreading layer described in Japanese Patent O.P.I. Publication No. 197466/1982, into the fiber constituting this spreading layer can be easily impregnated a desired amount of reagents.

The effect of this invention will not be reduced no matter which component layer of the analytical element of this invention contains the coupler.

The analytical reaction used in the analytical element of this invention may be settled according to the purpose for which it is used, and an aqueous fluid sample to be applied, whether it is a biological or nonbiological aqueous fluid sample, is acceptable as long as it contains hydrogen peroxide or a compound producing hydrogen peroxide. For example, it includes blood cells, blood plasma, blood serum, lymph, urine, and the like.

The analytical element of this invention, in addition to the foregoing peroxidase-functional material, hydrogen donor and coupler, may, according to the component to be analyzed, contain various reagents such as oxidase or other enzymes producing hydrogen peroxide, substrate, buffer, preservative, surfactant, hardening agent, etc.

The oxidase which produces hydrogen peroxide includes, for example, the following various ones: glucose oxidase, uricase, cholestrol oxidase, glycerol oxidase, glycerol-3-phosphoric acid oxidase, sarcosine oxidase, pyrubic acid oxidase, D-aspartic acid oxidase, D(or L)-amino acid oxidase, L-gulono-γ-lactone oxidase, L-sorbose oxidase, L-2-hydroxy acid oxidase, 6-hydroxy-D-nicotine oxidase, 6-hydroxy-L-nicotine oxidase, pyridoxaminephosphoric acid oxidase, pyridoxine oxidase, hexose oxidase, o-aminophenol oxidase, amine oxidase (containing pyridoxal or flavin), xanthin oxidase, alcohol oxidase, ethanolamine oxidase, $N^6$-methyl-L-lysine oxidase, α-glycerophosphate oxidase, choline oxdase, acyl CoA oxidase, sulfurous acid oxidase, and the like.

The analytical element of this invention may, if necessary, be of an arbitrary construction which meets the object of this invention and which comprises in combination of, e.g., reflective and subbing layers as described in U.S. Pat. No. 3,992,158; a radiation-blocking layer as described in U.S. Pat. No. 4,042,335; a barrier layer as described in U.S. Pat. No. 4,066,403; and a scavenger as described in Japanese Patent O.P. I. Publication No. 90859/1980.

These layers of the analytical element may be superposedly coated in an arbitrary thickness in order on a support of this invention in accordance with desired construction requirements by any one selected from the methods including the slide hopper coating method, extrusion coating method, dip coating method, and the like, which are well-known to the photographic field.

The thus composed analytical element of this invention, after a fluid sample is supplied thereto from the spreading layer side thereof, is observed with respect to the analytical reaction of the reagent layers from the transparent support side or from the reverse side thereto to measure the reflection density, and the measured value is applied to the calibration curve proposed in advance, whereby an unknown amount to be analyzed can be detected.

EXAMPLES

The following examples will further illustrate the present invention. The invention is not limited to and by the examples.

EXAMPLE 1

(Analytical element for use with glucose)

On a 180 μm-thick transparent polyethylene terephthalate support with subbing layer are provided one or two reagent layers of the compositions given in Table 1, and on the reagent layers is provided a spreading layer of the composition given in Table 2, whereby analytical elements 1 through 3 of this invention and a comparative analytical element 1 as shown in Table 3 are prepared.

TABLE 1

|  | Reagent layer | | | |
|---|---|---|---|---|
|  | R-1 | R-2 | R-3 | R-4 |
| 3,3-dimethyl-glutaric acid (g/m$^2$) | 2.8 | — | 2.8 | 2.8 |
| 4-aminoantipyrin (g/m$^2$) | — | 1.8 | — | — |
| 4-aminoantipyrin hydrochloride (g/m$^2$) | — | — | 2.2 | 2.2 |
| 1,7-dihydroxynaphthalene (g/m$^2$) | 1.4 | — | 1.4 | 1.4 |
| Dimedone (g/m$^2$) | 0.4 | — | 0.4 | 0.4 |
| Glucose oxidase (U/m$^2$) | 35,000 | — | 35,000 | 35,000 |
| Peroxidase (U/m$^2$) | 15,000 | — | — | 15,000 |
| Butyl acrylate-vinyl acetate copolymer(ratio bt wt 1:1) (g/m$^2$) | 23 | — | 23 | 23 |
| Gelatin (g/m$^2$) | 23 | — | 23 | 23 |
| Polyvinyl pyrrolidone (g/m$^2$) | — | 6 | — | — |
| Sodium triisopropylnaphthalene-sulfonate (g/m$^2$) | 0.6 | — | 0.6 | 0.6 |
| 1,2-bis(vinyl-sulfonyl) ethane (g/m$^2$) | 0.4 | — | 0.4 | 0.4 |

Note:
(1) R-2: n-butanol solution is coated.
(2) R-1, R-3 and R-4: The pH is adjusted to 6.1 by use of an aqueous NaOH solution.

TABLE 2

|  | Spreading layer | | |
|---|---|---|---|
|  | S-1 | S-2 | S-3 |
| Powder filter [Toyo Roshi K.K.; more than 300 mesh] (g/m$^2$) | 91 | 91 | 91 |
| Styrene-glycidylmethacrylate copolymer (ratio by wt 9:1) (g/m$^2$) | 13 | 13 | 13 |
| Triton ® X-100 (g/m$^2$) | 9 | 9 | 9 |
| 4-aminoantipyrin hydrochloride (g/m$^2$) | — | 2.2 | — |
| Peroxidase (U/m$^2$) | — | — | 15,000 |

Note:
(3) Xylene solvent is used in coating.
(4) Xylene is used separately as a solvent for 4-aminoantipyrin hydrochloride, which is directly dispersed thereinto by a sand grinder.
(5) The peroxidase is pulverized by a mortar, put through a 200-mesh screen, and then dispersed into the solvent.

TABLE 3

| Analytical element No. | Reagent layer-I | Reagent layer-II | Spreading layer |
|---|---|---|---|
| Invention's analytical element-1 | R-1 | R-2 | S-1 |
| Invention's analytical element-2 | R-1 | — | S-2 |
| Invention's analytical element-3 | R-3 | — | S-3 |
| Comparative analytical element-1 | R-4 | — | S-1 |

The above invention's analytical elements 1 through 3 and comparative analytical element-1 each was measured from its support side with respect to its reflection densities (fog) at 540 nm right after its preparation and after it was allowed to stand at 40° C. for three days and also its reflection densities at 540 nm after 100, 300 and 500 mg/dl of a glucose sandard liquid were added dropwise to its 10 μl spreading layer and it was kept at 37° C. for 10 minutes. Consequently the results as shown in Table 4 were obtained.

TABLE 4

| Glucose concentration | Right after preparation | | | | After 3-day storage | | | |
|---|---|---|---|---|---|---|---|---|
| (mg/dl) | (fog) | 100 | 300 | 500 | (fog) | 100 | 300 | 500 |
| Invention's analytical element-1 | 0.45 | 0.73 | 1.12 | 1.45 | 0.46 | 0.74 | 1.14 | 1.46 |
| Invention's analytical element-2 | 0.42 | 0.71 | 1.08 | 1.40 | 0.43 | 0.72 | 1.10 | 1.42 |
| Invention's analytical element-3 | 0.46 | 0.72 | 1.06 | 1.34 | 0.48 | 0.74 | 1.09 | 1.37 |
| Comparative analytical element-1 | 0.47 | 0.74 | 1.10 | 1.39 | 0.63 | 0.89 | 1.22 | 1.48 |

As is apparent from Table 4, the comparative analytical element-1, prepared so that both hydrogen donor, 4-aminoantipyrin hydrochloride and peroxidase are contained to be present together, shows remarkable increases in the fog and color density caused during its storage. In contrast, the analytical element samples each of this invention shows very small changes in the fog and color density even after its storage, and thus it is understood that the stability of the element is improved.

EXAMPLE 2

(Analytical element for use with cholesterol)

On a subbed 180 μm-thick transparent polyethylene terephthalate support are provided one or two reagent layers of the compositions as given in Table 5, and then on this is provided a spreading layer of the composition as given in Table 6, whereby an analytical element-4 of this invention and a comparative analytical element-2 as shown in Table 7 are prepared.

TABLE 5

| | Reagent layer | | |
|---|---|---|---|
| | R-5 | R-6 | R-7 |
| Dipotassium hydrogenphosphate (g/m$^2$) | 3.3 | — | 3.3 |
| Potassium dihydrogenphosphate (g/m$^2$) | 1.5 | — | 1.5 |
| 4-aminoantipyrin (g/m$^2$) | — | 1.1 | 1.1 |
| 1,7-dihydroxynaphthalene (g/m$^2$) | 1.0 | — | 1.0 |
| Dimedone (g/m$^2$) | 0.3 | — | 0.3 |
| Peroxidase (U/m$^2$) | 5000 | — | 5000 |
| Gelatin (g/m$^2$) | 25 | — | 25 |
| Polyvinyl pyrrolidone (g/m$^2$) | — | 5 | — |
| Sodium triisopropylnaphthalenesulfonate (g/m$^2$) | 0.5 | — | 0.5 |
| 1,2-bis(vinylsulfonyl)ethane (g/m$^2$) | 0.2 | — | 0.2 |

Note:
(6) R-6 is coated in the form of an n-butanol solution.

TABLE 6

| | Spreading layer S-4 |
|---|---|
| Powder filter [Toyo Roshi K.K. more than 300 mesh] (g/m$^2$) | 91 |
| Styrene-glycidylmethacrylate copolymer (ratio by wt 9:1) (g/m$^2$) | 13 |
| Triton ® X-100 (g/m$^2$) | 9 |
| Cholesterol esterase (U/m$^2$) | 6,000 |

TABLE 6-continued

| | Spreading layer S-4 |
|---|---|
| Cholesterol oxidase (U/m$^2$) | 6,000 |

Note:
(7) The cholesterol esterase and cholesterol oxidase are pulverized by a mortar, passed through a 200-mesh screen, and then dispersedly added.

TABLE 7

| | Reagent layer | | Spreading layer |
|---|---|---|---|
| Analytical element No. | Reagent layer-I | Reagent layer-II | |
| Invention's analytical element-4 | R-5 | R-6 | S-4 |
| Comparative analytical element-2 | R-7 | — | S-4 |

The above invention's analytical element-4 and comparative analytical element-2 each was measured from its support side with respect to its reflection densities (fog) at 540 nm right after its preparation and after it was allowed to stand at 40° C. for three days and also its reflection densities at 540 nm after 150, 300 and 450 mg/dl of a cholesterol standard liquid prepared from LIPID SERUM®-I and -II (produced by Eiken Kagaku K.K.) were added dropwise to its 10 μl spreading layer and it was kept at 37° C. for 10 minutes. Consequently, the results as shown in Table 8 were obtained.

TABLE 8

| Cholesterol | Right after preparation | | | | After 3-day storage | | | |
|---|---|---|---|---|---|---|---|---|
| concentration (mg/dl) | (fog) | 150 | 300 | 450 | (fog) | 150 | 300 | 450 |
| Invention's analytical element-4 | 0.41 | 0.91 | 1.15 | 1.32 | 0.42 | 0.92 | 1.15 | 1.33 |
| Comparative analytical element-2 | 0.43 | 0.93 | 1.13 | 1.28 | 0.58 | 1.06 | 1.24 | 1.36 |

As is apparent from Table 8, the comparative analytical element-2, prepared so that both hydrogen donor 4-aminoantipyrin and peroxidase are contained to be present together, shows conspicuously large increases in the fog and color density caused during its storage. In contrast, the analytical element of this invention shows very small changes in the fog and color density even after its storage, and thus it is understood that the stability of the element is improved.

EXAMPLE 3

(Analytical element for use with uric acid)

On a subbed 180 μm-thick transparent polyethylene terephthalate support is provided a reagent layer of the composition as given in Table 9, and on this reagent layer is further provided a spreading layer of the composition as given in Table 10, whereby an analytical element-5 of this invention and a comparative analytical element-3 as shown in Table 11 are prepared.

TABLE 9

| | Reagent layer | |
|---|---|---|
| | R-8 | R-9 |
| 1-(2,4,6-trichlorophenyl)-3-(2-chloro-5-octadecyl-succinimidoanilino)-5-pyrazolone (*9) (g/m$^2$) | 6.7 | 6.7 |
| N,N—diethyl-3-methanesulfonamidoethyl-4-aminoaniline p-toluenesulfonate (g/m$^2$) | — | 0.15 |
| Uricase (U/m$^2$) | 500 | 500 |
| Peroxidase (U/m$^2$) | 15,000 | 15,000 |
| Gelatin (*9) (g/m$^2$) | 13 | 13 |
| Butyl acrylate-vinyl acetate copolymer (ratio by wt 1:1) (g/m$^2$) | 12 | 12 |
| Sodium triisopropylnaphthalenesulfonate (*9) (g/m$^2$) | 1.2 | 1.2 |
| 1,2-bis(vinylsulfonyl)ethane (g/m$^2$) | 0.2 | 0.2 |

Note:
(*8) R-8 and R-9 each is coated after adjusting its pH to 8.5 by a borate buffer (boric acid-sodium hydroxide).
(*9) The 1-(2,4,6-trichlorophenyl)-3-(2-octadecylsuccinimidoanilino)-5-pyrazolone, after being dissolved into a mixture of ethyl-acetate and dibutylphthalate, is added to a mixture of sodium triisopropylnaphthalenesulfonate and an aqueous gelatin solution, and ultrasonically dispersed, and then used.

TABLE 10

| | Spreading layer | |
|---|---|---|
| | S-5 | S-6 |
| Powder filter [Toyo Roshi K.K., more than 300 mesh] (g/m$^2$) | 91 | 91 |
| N,N—diethyl-3-methanesulfonamidoethyl-4-aminoaline p-toluenesulfonate (g/m$^2$) | 0.15 | — |
| Styrene-glycidyl methacrylate copolymer (ratio by wt 9:1) (g/m$^2$) | 13 | 13 |
| Triton ® X-100 (g/m$^2$) | 9 | 9 |

Note:
(*10) The N,N—diethyl-3-methanesulfonamidoethyl-4-aminoaniline p-toluenesulfonate, after being dissolved in a methanol-xylene solvent, is stirred along with the powder filter added thereto to be impregnated into the powder filter, which is then filtered and dried to be used.

TABLE 11

| Analytical element No. | Reagent layer | Spreading layer |
|---|---|---|
| Invention's analytical element-5 | R-8 | S-5 |
| Comparative analytical element-3 | R-9 | S-6 |

The above invention's analytical element-5 and comparative analytical element-3 each was measured from its support side with respect to its reflection densities (fog) at 540 nm right after its preparation and after it was allowed to stand at 40° C. for three days and also its reflection densities at 540 nm after 5, 10 and 15 mg/dl of a uric acid standard liquid were added dropwise to its 10 μl spreading layer and it was kept at 37° C. for 10 minutes, whereby the results as shown in Table 12 were obtained.

TABLE 12

| Uric acid | Right after preparation | | | | After 3-day storage | | | |
|---|---|---|---|---|---|---|---|---|
| Concentration (mg/dl) | (fog) | 5 | 10 | 15 | (fog) | 5 | 10 | 15 |
| Invention's analytical element-5 | 0.47 | 0.66 | 0.89 | 1.08 | 0.50 | 0.69 | 0.91 | 1.09 |
| Comparative analytical element-3 | 0.59 | 0.85 | 1.05 | 1.19 | 0.81 | 1.08 | 1.25 | 1.37 |

As is apparent from the results shown in Table 2, the comparative analytical element-3, prepared so that both hydrogen donor N,N-diethyl-3-methanesulfonamidoethyl-4-aminoaniline p-toluenesulfonate and peroxidase are contained to be present together, shows conspicuously large increases in the fog and color density caused during its storage. In contrast, the analytical element of this invention shows very small changes in the fog and color density even after its storage, and thus it is understood that the stability of the element is improved.

EXAMPLE 4

(Analytical element for use with uric acid)

An analytical element-6 of this invention and a comparative analytical element-4 are prepared in quite the same manner as in Example 3 except that the 1-(2,4,6-trichlorophenyl)-3-(2-chloro-5-octadecylsuccinimidoanilino)-5-pyrazolone is replaced by 6.2 g/m$^2$ of 2-tetrafluoroethylcarbonylamino-5-[α-(2,4-di-t-amylphenoxy)pentyl-carbonylamino]phenol, and the N,N-diethyl-3-methanesulfonamidoethyl-4-aminoaniline p-toluenesulfonate is replaced by 0.13 g/m$^2$ of N-ethyl-N-methoxyethyl-3-methyl-4-aminoaniline p-toluenesulfonate.

The thus obtained analytical elements each was measured in quite the same manner as in Example 3 with respect to the reflection densities at 640 nm. As a result, the comparative analytical element shows remarkably large increases in the fog and color density caused during its storage, whereas the analytical element of this invention shows very small changes in the fog and color density even after its storage, and thus it is understood that the stability of the element of this invention is improved.

EXAMPLE 5

(Analytical element for use with triglyceride)

On a subbed 180 μm-thick transparent polyethylene terephthalate support are provided two reagent layers of the compositions given in Table 13, and on the layers is provided a spreading layer of the composition given in Table 14, whereby an analytical element-7 of this invention and a comparative analytical element-5 are prepared.

TABLE 13

| | Reagent layer | | | |
|---|---|---|---|---|
| | R-10 | R-11 | R-12 | R-13 |
| 1,7-dihydroxynaphthalene (g/m$^2$) | — | 2.0 | — | 2.0 |
| 4-aminoantipyrin (g/m$^2$) | — | 1.3 | 1.3 | — |
| Adenosine-5'-(sodium)triphosphate (g/m$^2$) | — | 3.3 | — | 3.3 |
| Glycerol kinase (U/m$^2$) | 2,000 | — | 2,000 | — |
| Glycerol-3-phosphoric acid oxidase (U/m$^2$) | 4,000 | — | 4,000 | — |
| Peroxidase (U/m$^2$) | 3,000 | — | 3,000 | — |
| Magnesium chloride (g/m$^2$) | 0.12 | — | 0.12 | — |
| Polyacrylamide (g/m$^2$) | 6 | — | 6 | — |
| Polyvinyl pyrrolidone (g/m$^2$) | — | 6 | — | 6 |
| Triton ® X-100 (g/m$^2$) | 0.2 | — | 0.2 | — |

Note:
(*11) R-10 and R-12 each is coated after adjusting its pH to 7.5 by a phosphate buffer.
(*12) R-11 and R-13 each is coated in the form of an n-butanol solution.

TABLE 14

| | Spreading layer S-7 |
|---|---|
| Powder filter [Toyo Roshi K.K., more than 300 mesh] (g/m$^2$) | 91 |

TABLE 14-continued

|  | Spreading layer S-7 |
|---|---|
| Styrene-glycidyl methacrylate copolymer (g/m$^2$) | 13 |
| Triton ® X-100 (g/m$^2$) | 9 |
| Magnesium chloride (g/m$^2$) | 0.2 |
| Lipoprotein lipase (U/m$^2$) | 8,000 |

Note:
(*13) The magnesium chloride and lipoprotein lipase each was pulverized by a mortar, passed through a 200-mesh screen, and then dispersedly added.

TABLE 15

| Analytical element No. | Reagent layer | | Spreading layer |
|---|---|---|---|
|  | Reagent layer-1 | Reagent layer-2 |  |
| Invention's analytical element-7 | R-10 | R-11 | S-7 |
| Comparative analytical element-5 | R-12 | R-13 | S-7 |

The above invention's analytical element-7 and comparative analytical element-5 each was measured from its support side with respect to its reflections densities (fog) at 540 nm right after its preparation and after it was allowed to stand at 40° C. for three days and also its reflection densities at 540 nm after 100, 200 and 300 mg/d of a triglyceride standard liquid, prepared with LIPID SERUM®-I and II (produced by Eiken Kagaku K.K.), were added dropwise to its 10 μl on spreading layer and it was kept at 37° C. for 10 minutes.

TABLE 16

| Triglyceride concentration (mg/dl) | Right after preparation | | | | After 3-day storage | | | |
|---|---|---|---|---|---|---|---|---|
|  | (fog) | 100 | 200 | 300 | (fog) | 100 | 200 | 300 |
| Invention's analytical element-7 | 0.46 | 0.64 | 0.82 | 0.99 | 0.47 | 0.66 | 0.83 | 1.00 |
| Comparative analytical element-5 | 0.48 | 0.65 | 0.81 | 0.95 | 0.62 | 0.80 | 0.94 | 1.04 |

As is apparent from the results shown in Table 16, the comparative analytical element-5, prepared so that both hydrogen donor 4-aminoantipyrin and peroxidase are contained to be present together, shows conspicuously large increases in the fog and color density caused during its storage, whereas the analytical element of this invention shows very small changes in the fog and color density even after its storage, and thus it is understood that the stability of the element of this invention is improved.

EXAMPLE 6
(Analytical element for use with triglyceride)

On a subbed 180 μm-thick transparent polyethylene terephthalate support are provided one or two reagent layers of the compositions given in Table 17, on which is further provided a spreading layer of the composition given in Table 18, whereby an analytical element-8 of this invention and a comparative analytical element-6 are prepared.

TABLE 17

|  | Reagent layer | | |
|---|---|---|---|
|  | R-14 | R-15 | R-16 |
| 1,7-dihydroxynaphthalene (g/m$^2$) | 1.5 | — | 1.5 |
| 4-aminoantipyrin (g/m$^2$) | — | 1.3 | 1.3 |
| Glycerol oxidase (U/m$^2$) | 5,000 | — | 5,000 |
| Peroxidase (U/m$^2$) | 10,000 | — | 10,000 |
| Gelatin (g/m$^2$) | 23 | — | 23 |
| Polyvinyl pyrrolidone (g/m$^2$) | — | 5 | — |
| Triton ® X-100 (g/m$^2$) | 0.2 | — | 0.2 |

TABLE 17-continued

|  | Reagent layer | | |
|---|---|---|---|
|  | R-14 | R-15 | R-16 |
| 1,2-bis(vinylsulfonyl)ethane (g/m$^2$) | 0.2 | — | 0.2 |

Note:
(*14) R-14 and R-16 each is coated after adjusting its pH to 8.0 with a phosphate buffer.
(*15) R-15 is coated in the form of an n-butanol solution.

TABLE 18

|  | Spreading layer S-8 |
|---|---|
| Powder filter [Toyo Roshi K.K., more than 300 mesh] (g/m$^2$) | 91 |
| Styrene-glycidyl methacrylate copolymer (g/m$^2$) | 13 |
| Triton ® X-100 (g/m$^2$) | 9 |
| Lipoprotein lipase (U/m$^2$) | 15,000 |

Note:
(*16) The lipoprotein lipase is pulverized by mortar, put through a 200-mesh screen, and then dispersedly added.

TABLE 19

| Analytical element No. | Reagent layer | | Spreading layer |
|---|---|---|---|
|  | Reagent layer-I | Reagent layer-II |  |
| Invention's analytical element-8 | R-14 | R-15 | S-8 |
| Comparative analytical element-6 | R-16 | — | S-8 |

The above analytical element-8 of this invention and comparative analytical element-6 each was measured in quite the same manner as in Example 5 with respect to the reflection densities. Consequently, the comparative analytical element shows remarkable increases in the fog and color density caused during its storage, whereas the analytical element of this invention shows very small changes in the fog and color density even after its storage, and thus it is understood that the stability of the element of this invention is improved.

As has been described in detail above, the analytical element of this invention is very effective and useful in respect that it is an analytical element for the detection of hydrogen peroxide excellent in the quantitative sensitivity as well as in the accuracy of measurement and also excellent in the preservability.

What is claimed is:

1. In a multilayered analytical element for detecting hydrogen peroxide which comprises peroxidase-functional material, a hydrogen donor and a coupler, the improvement comprising arranging said peroxidase-functional material and said hydrogen donor in different layers in a manner so that they are separated from each other but are capable of interacting when a liquid sample is applied to the analytical element.

2. The analytical element of claim 1, wherein said hydrogen donor is selected from the group consisting of 4-substituted antipyrine compounds, 2-hydrazonobenzothiazoline compounds, p-halogenophenol compounds, and o- and p-phenylene diamine compounds.

3. The analytical element of claim 1, wherein said coupler is selected from the group consisting of acylacetoamide compounds, pyrazolone compounds, phenol compounds, naphthol compounds and N,N-disubstituted aniline compounds.

4. The analytical element of claim 1, wherein said analytical element comprises a support, and wherein one of said layers is a spreading layer.

5. The analytical element of claim 4, wherein one of said peroxidase-functional material and said hydrogen donor is contained in said spreading layer.

6. The analytical element of claim 1, wherein the content of said peroxidase-functional material is in the range of 100 U/m$^2$ to 1,000,000 U/m$^2$.

7. The analytical element of claim 6, wherein the content of said peroxidase-functional material is in the range of 1,000 U/m$^2$ to 100,000 U/m$^2$.

8. The analytical element of claim 1, wherein the content of said hydrogen donor is in the range of 0.01 m mol/m$^2$ to 100 m mol/m$^2$.

9. The analytical element of claim 8, wherein the content of said hydrogen donor is in the range of 0.05 m mol/m$^2$ to 50 m mol/m$^2$.

10. The analytical element of claim 1, wherein the content of said coupler is in the range of 0.1 m mol/m$^2$ to 100 m mol/m$^2$.

11. The analytical element of claim 10, wherein the content of said coupler is in the range of 0.5 m mol/m$^2$ to 50 m mol/m$^2$.

* * * * *